(12) United States Patent
Jenkins et al.

(10) Patent No.: US 7,825,087 B2
(45) Date of Patent: Nov. 2, 2010

(54) NANOPARTICULATE AND CONTROLLED RELEASE COMPOSITIONS COMPRISING CYCLOSPORINE

(75) Inventors: Scott A. Jenkins, Downingtown, PA (US); Gary Liversidge, Westchester, PA (US)

(73) Assignee: Elan Pharma International Limited, County Westmeath (IE)

( * ) Notice: Subject to any disclaimer, the term of this patent is extended or adjusted under 35 U.S.C. 154(b) by 207 days.

(21) Appl. No.: 11/568,692

(22) PCT Filed: Apr. 12, 2006

(86) PCT No.: PCT/US2006/013631

§ 371 (c)(1),
(2), (4) Date: Aug. 22, 2007

(87) PCT Pub. No.: WO2006/110802

PCT Pub. Date: Oct. 19, 2006

(65) Prior Publication Data

US 2008/0124389 A1    May 29, 2008

Related U.S. Application Data

(60) Provisional application No. 60/670,836, filed on Apr. 13, 2005.

(51) Int. Cl.
   *A61K 38/12*   (2006.01)
   *A61K 51/08*   (2006.01)

(52) U.S. Cl. .............................. 514/9; 514/11; 530/317; 424/1.13

(58) Field of Classification Search ........................ None
See application file for complete search history.

(56) References Cited

U.S. PATENT DOCUMENTS

| | | |
|---|---|---|
| 4,783,484 A | 11/1988 | Violante et al. |
| 4,826,689 A | 5/1989 | Violante et al. |
| 4,997,454 A | 3/1991 | Violante et al. |
| 5,145,684 A | 9/1992 | Liversidge et al. |
| 5,298,262 A | 3/1994 | Na et al. |
| 5,302,401 A | 4/1994 | Liversidge et al. |
| 5,318,767 A | 6/1994 | Liversidge et al. |
| 5,326,552 A | 7/1994 | Na et al. |
| 5,328,404 A | 7/1994 | Bacon |
| 5,336,507 A | 8/1994 | Na et al. |
| 5,340,564 A | 8/1994 | Illig et al. |
| 5,346,702 A | 9/1994 | Na et al. |
| 5,349,957 A | 9/1994 | Yudelson |
| 5,352,459 A | 10/1994 | Hollister et al. |
| 5,399,363 A | 3/1995 | Liversidge et al. |
| 5,401,492 A | 3/1995 | Kellar et al. |
| 5,429,824 A | 7/1995 | June |
| 5,447,710 A | 9/1995 | Na et al. |
| 5,451,393 A | 9/1995 | Liversidge et al. |
| 5,466,440 A | 11/1995 | Ruddy et al. |
| 5,470,583 A | 11/1995 | Na et al. |
| 5,472,683 A | 12/1995 | Illig |
| 5,494,683 A | 2/1996 | Liversidge et al. |
| 5,500,204 A | 3/1996 | Osifo |
| 5,510,118 A | 4/1996 | Bosch et al. |
| 5,518,187 A | 5/1996 | Bruno et al. |
| 5,518,738 A | 5/1996 | Eickhoff et al. |
| 5,521,218 A | 5/1996 | Osifo |
| 5,525,328 A | 6/1996 | Bacon et al. |
| 5,534,270 A | 7/1996 | De Castro |
| 5,543,133 A | 8/1996 | Swanson et al. |
| 5,552,160 A | 9/1996 | Liversidge et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,749 A | 11/1996 | Illig |
| 5,573,750 A | 11/1996 | Singh |
| 5,573,783 A | 11/1996 | Desieno et al. |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,593,657 A | 1/1997 | Ruddy et al. |
| 5,622,938 A | 4/1997 | Wong |
| 5,628,981 A | 5/1997 | Liversidge et al. |
| 5,643,552 A | 7/1997 | Illig |
| 5,662,883 A | 9/1997 | Bagchi et al. |
| 5,665,331 A | 9/1997 | Bagchi et al. |

(Continued)

FOREIGN PATENT DOCUMENTS

WO    9836736    8/1998

OTHER PUBLICATIONS

Chen, 2002, International Journal of Pharmaceutics, 242, 3-14.*
Chen et al., Preparation of cyclosporine A nanoparticles by evaporative precipitation into aqueous solution, Int'l Journal of Pharm., 242: 3-14 (2002).

*Primary Examiner*—Andrew D Kosar
*Assistant Examiner*—Satyanarayana R Gudibande
(74) *Attorney, Agent, or Firm*—Fox Rothschild LLP

(57) ABSTRACT

The present invention is directed to a composition comprising a nanoparticulate cyclosporine having improved bioavailability. The nanoparticulate cyclosporine particles of the composition have an effective average particle size of less than about 2000 nm in diameter and are useful in the prevention and treatment of organ transplant rejection and autoimmune diseases such as psoriasis, rheumatoid arthritis, and other related diseases. The invention also relates to a controlled release composition comprising a cyclosporine or a nanoparticulate cyclosporine that in operation delivers the drug in a pulsed or bimodal manner for the prevention and treatment of organ transplant rejection and autoimmune diseases such as psoriasis, rheumatoid arthritis, and other related diseases.

16 Claims, No Drawings

U.S. PATENT DOCUMENTS

| | | |
|---|---|---|
| 5,718,388 A | 2/1998 | Czekai et al. |
| 5,718,919 A | 2/1998 | Ruddy et al. |
| 5,741,522 A | 4/1998 | Violante et al. |
| 5,747,001 A | 5/1998 | Wiedmann et al. |
| 5,756,450 A | 5/1998 | Hahn et al. |
| 5,759,997 A | 6/1998 | Cavanak |
| 5,766,629 A | 6/1998 | Cho et al. |
| 5,776,496 A | 7/1998 | Violante et al. |
| 5,827,822 A | 10/1998 | Floc'h et al. |
| 5,834,017 A | 11/1998 | Cho et al. |
| 5,834,025 A | 11/1998 | Garavilla et al. |
| 5,862,999 A | 1/1999 | Czekai et al. |
| 5,962,019 A | 10/1999 | Cho et al. |
| 5,977,066 A | 11/1999 | Cavanak |
| 6,045,829 A | 4/2000 | Liversidge et al. |
| 6,068,858 A | 5/2000 | Liversidge et al. |
| 6,153,225 A | 11/2000 | Lee et al. |
| 6,165,506 A | 12/2000 | Jain et al. |
| 6,221,400 B1 | 4/2001 | Liversidge et al. |
| 6,239,124 B1 | 5/2001 | Zenke et al. |
| 6,254,885 B1 | 7/2001 | Cho et al. |
| 6,264,922 B1 | 7/2001 | Wood et al. |
| 6,267,989 B1 | 7/2001 | Liversidge et al. |
| 6,270,806 B1 | 8/2001 | Liversidge et al. |
| 6,306,825 B1 | 10/2001 | Cavanak |
| 6,316,029 B1 | 11/2001 | Jain et al. |
| 6,358,425 B1 | 3/2002 | King et al. |
| 6,375,986 B1 | 4/2002 | Ryde et al. |
| 6,428,814 B1 | 8/2002 | Bosch |
| 6,431,478 B1 | 8/2002 | Reed et al. |
| 6,432,381 B2 | 8/2002 | Liversidge et al. |
| 6,432,445 B1 | 8/2002 | Ambuhl et al. |
| 6,455,518 B2 | 9/2002 | Zenke et al. |
| 6,468,968 B2 | 10/2002 | Cavanak et al. |
| 6,475,519 B1 | 11/2002 | Meinzer et al. |
| 6,486,124 B2 | 11/2002 | Olbrich et al. |
| 6,582,718 B2 | 6/2003 | Kawashima et al. |
| 6,620,325 B2 | 9/2003 | Fuenfschilling et al. |
| 6,656,504 B1 * | 12/2003 | Bosch et al. ................ 424/489 |
| 6,723,339 B2 | 4/2004 | Meinzer et al. |
| 6,730,325 B2 * | 5/2004 | Devane et al. .............. 424/489 |
| 2002/0012675 A1 | 1/2002 | Jain et al. |
| 2002/0016290 A1 | 2/2002 | Floc'h et al. |
| 2004/0156895 A1* | 8/2004 | Pruitt et al. ................. 424/465 |

* cited by examiner

NANOPARTICULATE AND CONTROLLED RELEASE COMPOSITIONS COMPRISING CYCLOSPORINE

FIELD OF INVENTION

The present invention relates to a novel composition for use in prevention and treatment of organ transplant rejection and autoimmune diseases such as psoriasis, rheumatoid arthritis, and other related diseases and methods for making and using the composition. The composition comprises cyclosporine. The cyclosporine may exist in nanoparticulate form, that is in particles having an effective average particle size of less than 2000 nm in diameter. The composition may be formulated to allow for controlled release of the cyclosporine.

BACKGROUND OF INVENTION

A. Background Regarding Cyclosporine

The compositions of the invention comprise a cyclosporine. Cyclosporines are a large class of peptide compounds having pharmaceutical utility, for example immunosuppressant, anti-inflammatory, and/or anti-parasitic activity and/or activity in abrogating tumor resistance to anti-neoplastic or cytostatic drug therapy. Cyclosporine is a cyclic non-ribosomal polypeptide immunosuppressant agent consisting of 11 amino acids. It is produced as a metabolite by the ascomycete fungus *Beauveria nivea*. The cyclosporines include, for example, naturally occurring fungal metabolites, such as the cyclosporine A, B, C, D and G, as well as a wide variety of synthetic and semi-synthetic cyclosporines, for example the dihydro- and iso-cyclosporines.

Cyclosporines have been described in, for example, U.S. Pat. Nos. 5,756,450 for "Water Soluble Monoesters as Solubisers for Pharmacologically Active Compounds and Pharmaceutical Excipients and Novel Cyclosporine Galenic Forms;" 5,759,997 for "Cyclosporin Galenic Forms; 5,977,066 for "Cyclosporin Galenic Forms"; 6,239,124 for "Pharmaceutical Compositions for the Treatment of Transplant Rejection or Autoimmune or Inflammatory Conditions Comprising Cyclosporin A and 40-O-(2-hydroxyethyl)-rapamycin;" 6,262,022 for "Pharmaceutical Compositions Containing Cyclosporin as the Active Agent;" 6,306,825 for "Cyclosporin Galenic Forms;" 6,432,445 for "Pharmaceutical Capsules Comprising a Cyclosporin;" 6,455,518 for "Pharmaceutical Compositions for the Treatment of Transplant Rejection or Autoimmune or Inflammatory Conditions Comprising Cyclosporin A and 40-0-(2-hydroxyethyl)-rapamycin;" 6,468,968 for "Cyclosporin Galenic Forms"; 6,475,519 for "Oil-free Pharmaceutical Compositions Containing Cyclosporin A;" 6,486,124 for "Cyclosporin Compositions and Processes Therefor;" 6,582,718 for "Cyclosporin Compositions;' 6,620,325 for "Purification Process for Cyclosporin;" and 6,723,339 for "Oil-free Pharmaceutical Compositions Containing Cyclosporin A."

Cyclosporine has been demonstrated to suppress some humoral immunity and, to a greater extent, cell-mediated reactions such as allograft rejection, delayed hypersensitivity, experimental allergic encephalomyelitis, Freund's adjuvant arthritis, and graft versus host disease in many animal species for a variety of organs. It has been used post-allogenic organ transplant to reduce the activity of the patient's immune system to lower the risk of organ rejection in the case of transplants of skin, heart, kidney, lung, pancreas, bone marrow and small intestine.

Apart from transplant medicine, cyclosporine is also used in treating psoriasis and rheumatoid arthritis and related diseases, although only in severe cases, and has been investigated for use in treating many other autoimmune disorders. It is often taken in conjunction with corticosteroids. More recently, cyclosporine has been used successfully in treating patients suffering from ulcerative colitis.

Experimental evidence suggests that the effectiveness of cyclosporine is due to specific and reversible inhibition of immunocompetent lymphocytes in the $G_0$- or $G_1$-phase of the cell cycle. T-lymphocytes are preferentially inhibited. The T-helper cell is the main target, although the T-suppressor cell may also be suppressed. Cyclosporine also inhibits lymphokine production and release including interleukin-2 or T-cell growth factor (TCGF). Cyclosporine is thought to bind to the cytosolic protein cyclophilin (immunophilin) of immunocompetent lymphocytes, especially T-lymphocytes. This complex of cyclosporin and cyclophylin inhibits calcineurin, which under normal circumstances is responsible for activating the transcription of interleukin-2. It also inhibits lymphokine production and interleukin release and therefore leads to a reduced function of effector T-cells. No functional effects on phagocytic (changes in enzyme secretions not altered, chemotactic migration of granulocytes, macrophage migration, carbon clearance in vivo) or tumor cells (growth rate, metastasis) can be detected in animals. Cyclosporine does not cause bone marrow suppression in animal models or man.

Chemically, cyclosporine is designated as [R—[R*,R*-(E)]]-cyclic (L-alanyl-D-alanyl-N-methyl-L-leucyl-N-methyl-L-leucyl-N-methyl-L-valyl-3-hydroxy-N,4-dimethyl-L-2-amino-6-octenoyl-L-(alpha)-amino-butyryl-N-methylglycyl-N-methyl-L-leucyl-L-valyl-N-methyl-L-leucyl). The molecular formula of cyclosporine is $C_{62}H_{111}N_{11}O_{12}$ with a molecular weight of 1202.63. The chemical structure of cyclosporine (also known as cyclosporin A) is:

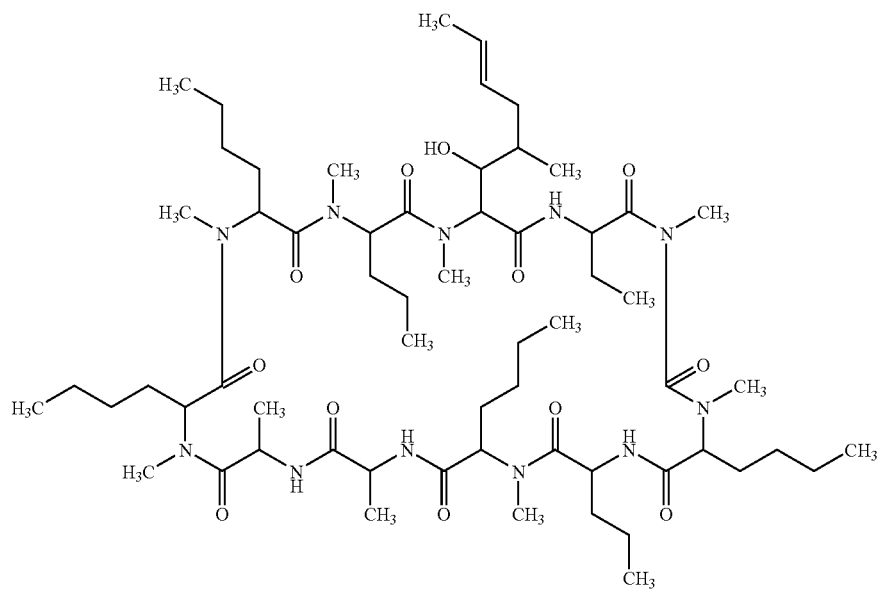

The drug is sold by Novartis under the brand names SAND-IMMUNE® and NEORAL®. NEORAL® and SANDIMMUNE® differ in that NEORAL® has increased bioavailability compared to SANDIMMUNE®. Adjunct therapy with adrenal corticosteroids is recommended. Generic cyclosporine drugs have been produced by companies such as Sangstat, Abbott Laboratories and Gengraf. A topical emulsion of cyclosporine for treating keratoconjunctivitis sicca has been marketed under the trade name RESTASIS®.

The absorption of cyclosporine from the gastrointestinal tract is incomplete and variable. Peak concentrations ($C_{max}$) in blood and plasma are achieved at about 3.5 hours. $C_{max}$ and area under the plasma or blood concentration/time curve (AUC) increase with the administered dose; for blood the relationship is curvilinear (parabolic) between 0 and 1400 mg. $C_{max}$ is approximately 1.0 ng/mL/mg of dose for plasma and 2.7-1.4 ng/mL/mg of dose for blood (for low to high doses). Compared to an intravenous infusion, the absolute bioavailability of the oral solution is approximately 30% based upon the results in 2 patients.

Cyclosporine is distributed largely outside the blood volume. In blood the distribution is concentration dependent. Approximately 33%-47% is in plasma, 4%-9% in lymphocytes, 5%-12% in granulocytes, and 41%-58% in erythrocytes. At high concentrations, the uptake by leukocytes and erythrocytes becomes saturated. In plasma, approximately 90% is bound to proteins, primarily lipoproteins.

Cyclosporines are of high therapeutic value for the prevention of organ transplant rejection, and the treatment of autoimmune diseases, such as psoriasis and rheumatoid arthritis. However, cyclosporines present highly specific difficulties in relation to administration including in particular problems of stability, drug bioavailability, and variability in inter- and intra-patient dose response. In addition, because cyclosporine is practically insoluble in water, conventional cyclosporine tablets dissolve the drug in potentially toxic co-solvents, for example, propylene glycol. The daily dose of cyclosporine must be given in two divided doses, and should be administered on a consistent schedule with regard to time of day and in relation to meals.

Thus, there is a need in the art for cyclosporine compositions which overcome these and other problems associated with their use. The present invention then relates to a composition for the controlled release of a cyclosporine. The present invention also relates to a nanoparticulate formulation of cyclosporine having improved bioavailability. The present invention also relates to a composition for the controlled release of a nanoparticulate cyclosporine. In particular, the present invention relates to controlled release compositions that in operation deliver a cyclosporine in a pulsatile or in a constant zero order manner or an immediate release nanoparticulate composition with improved bioavailability. The present invention further relates to solid oral dosage forms containing such a controlled release or immediate release composition.

B. Background Regarding Nanoparticulate Compositions

Nanoparticulate compositions, first described in U.S. Pat. No. 5,145,684 ("the '684 patent"), are particles consisting of a poorly soluble therapeutic or diagnostic agent having adsorbed onto the surface thereof a non-crosslinked surface stabilizer. The '684 patent does not describe nanoparticulate compositions of cyclosporines.

Methods of making nanoparticulate compositions are described in, for example, U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate compositions are also described, for example, in U.S. Pat. Nos. 5,298,262 for "Use of Ionic Cloud Point Modifiers to Prevent Particle Aggregation During Sterilization;" 5,302,401 for "Method to Reduce Particle Size Growth During Lyophilization;" 5,318,767 for "X-Ray Contrast Compositions Useful in Medical Imaging;" 5,326,552 for "Novel Formulation For Nanoparticulate X-Ray Blood Pool Contrast Agents Using High Molecular Weight Nonionic Surfactants;" 5,328,404 for "Method of X-Ray Imaging Using Iodinated Aromatic Propanedioates;" 5,336,507 for "Use of Charged Phospholipids to Reduce Nanoparticle Aggregation;" 5,340,564 for "Formulations Comprising Olin 10-G to Prevent Particle Aggregation and Increase Stability;" 5,346,702 for "Use of Non-Ionic Cloud Point Modifiers to Minimize Nanoparticulate Aggregation During Sterilization;" 5,349,957 for "Preparation and Magnetic Properties of Very Small Magnetic-Dextran Particles;" 5,352,459 for "Use of Purified Surface Modifiers to Prevent Particle Aggregation During Sterilization;" 5,399,363 and 5,494,683, both for "Surface Modified Anticancer Nanoparticles;" 5,401,492 for "Water Insoluble Non-Magnetic Manganese Particles as Magnetic Resonance Enhancement Agents;" 5,429,824 for "Use of Tyloxapol as a Nanoparticulate Stabilizer;" 5,447,710 for "Method for Making Nanoparticulate X-Ray Blood Pool Contrast Agents Using High Molecular Weight Non-ionic Surfactants;" 5,451,393 for "X-Ray Contrast Compositions Useful in Medical Imaging;" 5,466,440 for "Formulations of Oral Gastrointestinal Diagnostic X-Ray Contrast Agents in Combination with Pharmaceutically Acceptable Clays;" 5,470,583 for "Method of Preparing Nanoparticle Compositions Containing Charged Phospholipids to Reduce Aggregation;" 5,472,683 for "Nanoparticulate Diagnostic Mixed Carbamic Anhydrides as X-Ray Contrast Agents for Blood Pool and Lymphatic System Imaging;" 5,500,204 for "Nanoparticulate Diagnostic Dimers as X-Ray Contrast Agents for Blood Pool and Lymphatic System Imaging;" 5,518,738 for "Nanoparticulate NSAID Formulations;" 5,521,218 for "Nanoparticulate Iododipamide Derivatives for Use as X-Ray Contrast Agents;" 5,525,328 for "Nanoparticulate Diagnostic Diatrizoxy Ester X-Ray Contrast Agents for Blood Pool and Lymphatic System Imaging;" 5,543,133 for "Process of Preparing X-Ray Contrast Compositions Containing Nanoparticles;" 5,552,160 for "Surface Modified NSAID Nanoparticles;" 5,560,931 for "Formulations of Compounds as Nanoparticulate Dispersions in Digestible Oils or Fatty Acids;" 5,565,188 for "Polyalkylene Block Copolymers as Surface Modifiers for Nanoparticles;" 5,569,448 for "Sulfated Non-ionic Block Copolymer Surfactant as Stabilizer Coatings for Nanoparticle Compositions;" 5,571,536 for "Formulations of Compounds as Nanoparticulate Dispersions in Digestible Oils or Fatty Acids;" 5,573,749 for "Nanoparticulate Diagnostic Mixed Carboxylic Anydrides as X-Ray Contrast Agents for Blood Pool and Lymphatic System Imaging;" 5,573,750 for "Diagnostic Imaging X-Ray Contrast Agents;" 5,573,783 for "Redispersible Nanoparticulate Film Matrices With Protective Overcoats;" 5,580,579 for "Site-specific Adhesion Within the GI Tract Using Nanoparticles Stabilized by High Molecular Weight, Linear Poly(ethylene Oxide) Polymers;" 5,585,108 for "Formulations of Oral Gastrointestinal Therapeutic Agents in Combination with Pharmaceutically Acceptable Clays;" 5,587,143 for "Butylene Oxide-Ethylene Oxide Block Copolymers Surfactants as Stabilizer Coatings for Nanoparticulate Compositions;" 5,591,456 for "Milled Naproxen with Hydroxypropyl Cellulose as Dispersion Stabilizer;" 5,593,657 for "Novel Barium Salt Formulations Stabilized by Non-ionic and Anionic Stabilizers;" 5,622,938 for "Sugar Based Surfactant for Nanocrystals;" 5,628,981 for "Improved Formulations of Oral Gastrointestinal Diagnostic X-Ray Contrast Agents and Oral Gastrointestinal Therapeutic Agents;" 5,643,552 for "Nanoparticulate Diagnostic Mixed Carbonic Anhydrides as X-Ray Contrast Agents for Blood Pool and Lymphatic System Imaging;" 5,718,388 for "Continuous Method of Grinding Pharmaceutical Substances;" 5,718,919 for "Nanoparticles Containing the R(−)Enantiomer of Ibuprofen;" 5,747,001 for "Aerosols Containing Beclomethasone Nanoparticle Dispersions;" 5,834,025 for "Reduction of Intravenously Administered Nanoparticulate Formulation Induced Adverse Physiological Reactions;" 6,045,829 "Nanocrystalline Formulations of Human Immunodeficiency Virus (HIV) Protease Inhibitors Using Cellulosic Surface Stabilizers;" 6,068,858 for "Methods of Making Nanocrystalline Formulations of Human Immunodeficiency Virus (HIV) Protease Inhibitors Using Cellulosic Surface Stabilizers;" 6,153,225 for "Injectable Formulations of Nanoparticulate Naproxen;" 6,165,506 for "New Solid Dose Form of Nanoparticulate Naproxen;" 6,221,400 for "Methods of Treating Mammals Using Nanocrystalline Formulations of Human Immunodeficiency Virus (HIV) Protease Inhibitors;" 6,264,922 for "Nebulized Aerosols Containing Nanoparticle Dispersions;" 6,267,989 for "Methods for Preventing Crystal Growth and Particle Aggregation in Nanoparticle Compositions;" 6,270,806 for "Use of PEG-Derivatized Lipids as Surface Stabilizers for Nanoparticulate Compositions;" 6,316,029 for "Rapidly Disintegrating Solid Oral Dosage Form," 6,375,986 for "Solid Dose Nanoparticulate Compositions Comprising a Synergistic Combination of a Polymeric Surface Stabilizer and Dioctyl Sodium Sulfosuccinate;" 6,428,814 for "Bioadhesive Nanoparticulate Compositions Having Cationic Surface Stabilizers;" 6,431,478 for "Small Scale Mill;" and 6,432,381 for "Methods for Targeting Drug Delivery to the Upper and/or Lower Gastrointestinal Tract," all of which are specifically incorporated by reference. In addition, U.S. Patent Application No. 20020012675 A1, published on Jan. 31, 2002, for "Controlled Release Nanoparticulate Compositions," describes nanoparticulate compositions, and is specifically incorporated by reference.

Amorphous small particle compositions are described, for example, in U.S. Pat. Nos. 4,783,484 for "Particulate Composition and Use Thereof as Antimicrobial Agent;" 4,826,689 for "Method for Making Uniformly Sized Particles from Water-Insoluble Organic Compounds;" 4,997,454 for "Method for Making Uniformly-Sized Particles From Insoluble Compounds;" 5,741,522 for "Ultrasmall, Non-aggregated Porous Particles of Uniform Size for Entrapping Gas Bubbles Within and Methods;" and 5,776,496, for "Ultrasmall Porous Particles for Enhancing Ultrasound Back Scatter."

Because cyclosporine is practically insoluble in water, significant bioavailability can be problematic. There is a need in the art for nanoparticulate cyclosporine formulations which overcome this and other problems associated with the use of cyclosporine in the prevention and treatment of organ transplant rejection and autoimmune diseases such as psoriasis, rheumatoid arthritis, and other related diseases. The present invention satisfies this need.

The present invention then, relates to a nanoparticulate cyclosporine composition for the prevention and treatment of organ transplant rejection and autoimmune diseases such as psoriasis, rheumatoid arthritis, and other related diseases. As described herein, the present invention further relates to controlled release composition comprising such a nanoparticulate cyclosporine.

DESCRIPTION OF THE INVENTION

The present invention relates to a nanoparticulate composition comprising cyclosporine. The composition comprises nanoparticulate cyclosporine particles and at least one surface stabilizer adsorbed on the surface of the cyclosporine particles. The nanoparticulate cyclosporine particles have an effective average particle size of less than about 2,000 nm in diameter.

A preferred dosage form of the invention is a solid dosage form, although any pharmaceutically acceptable dosage form can be utilized.

Another aspect of the invention is directed to a pharmaceutical composition comprising nanoparticulate cyclosporine particles and at least one surface stabilizer, a pharmaceutically acceptable carrier, as well as any desired excipients.

Another aspect of the invention is directed to a nanoparticulate cyclosporine composition, having an improved pharmacokinetic profile as compared to conventional cyclosporine formulations.

Another embodiment of the invention is directed to a nanoparticulate cyclosporine composition comprising one or more additional compounds useful in the prevention and treatment of organ transplant rejection and autoimmune diseases such as psoriasis, rheumatoid arthritis, and other related diseases.

This invention further discloses a method of making the inventive nanoparticulate cyclosporine composition. Such a method comprises contacting the nanoparticulate cyclosporine with at least one surface stabilizer for a time and under conditions sufficient to provide a stabilized nanoparticulate cyclosporine composition.

The present invention is also directed to methods of treatment including but not limited to, the prevention and treatment of organ transplant rejection and autoimmune diseases such as psoriasis, rheumatoid arthritis, and other related diseases using the novel nanoparticulate cyclosporine composition disclosed herein. Such methods comprise administering to a subject a therapeutically effective amount of a nanoparticulate cyclosporine. Other methods of treatment using the nanoparticulate compositions of the invention are known to those of skill in the art.

The present invention further relates to a controlled release composition comprising a cyclosporine or a nanoparticulate cyclosporine which in operation produces a plasma profile substantially similar to the plasma profile produced by the administration of two or more immediate release (IR) dosage forms given sequentially.

Conventional frequent dosage regimes in which an IR dosage form is administered at periodic intervals typically give rise to a pulsatile plasma profile. In this case, a peak in the plasma drug concentration is observed after administration of each IR dose with troughs (regions of low drug concentration) developing between consecutive administration time points. Such dosage regimes (and their resultant pulsatile plasma profiles) have particular pharmacological and therapeutic effects associated with them. For example, the wash out period provided by the fall off of the plasma concentration of the active agent between peaks has been thought to be a contributing factor in reducing or preventing patient tolerance to various types of drugs.

The present invention further relates to a controlled release composition comprising cyclosporine or a nanoparticulate cyclosporine which in operation produces a plasma profile that eliminates the "peaks" and "troughs" produced by the administration of two or more IR dosage forms given sequentially if such a profile is beneficial. This type of profile can be obtained using a controlled release mechanism that allows for "zero-order" delivery.

Multiparticulate modified controlled release compositions similar to those disclosed herein are disclosed and claimed in the U.S. Pat. Nos. 6,228,398 and 6,730,325 to Devane et al; both of which are incorporated by reference herein. All of the relevant prior art in this field may also be found therein.

It is a further object of the invention to provide a controlled release composition which in operation delivers a cyclosporine or a nanoparticulate cyclosporine in a pulsatile manner or a zero-order manner.

Another object of the invention is to provide a controlled release composition which substantially mimics the pharmacological and therapeutic effects produced by the administration of two or more IR dosage forms given sequentially.

Another object of the invention is to provide a controlled release composition which substantially reduces or eliminates the development of patient tolerance to a cyclosporine or a nanoparticulate cyclosporine present in the composition.

Another object of the invention is to provide a controlled release composition in which a first portion of the composition, i.e., a cyclosporine or a nanoparticulate cyclosporine, is released immediately upon administration and a second portion of the active ingredient is released rapidly after an initial delay period in a bimodal manner.

Another object of the invention is to formulate the dosage in the form of an erodable formulation, a diffusion controlled formulation, or an osmotic controlled formulation.

Another object of the invention is to provide a controlled release composition capable of releasing a cyclosporine or a nanoparticulate cyclosporine, in a bimodal or multi-modal manner in which a first portion of the active is released either immediately or after a delay time to provide a pulse of drug release and one or more additional portions of the cyclosporine or a nanoparticulate cyclosporine is released, after a respective lag time, to provide additional pulses of drug release during a period of up to twenty-four hours.

Another object of the invention is to provide solid oral dosage forms comprising a controlled release composition comprising a cyclosporine or a nanoparticulate cyclosporine.

Other objects of the invention include provision of a once daily dosage form of a cyclosporine or a nanoparticulate cyclosporine which, in operation, produces a plasma profile substantially similar to the plasma profile produced by the administration of two immediate release dosage forms given sequentially and a method for prevention and treatment of organ transplant rejection and autoimmune diseases such as psoriasis, rheumatoid arthritis, and other related diseases based on the administration of such a dosage form.

The above objects are realized by a controlled release composition having a first component comprising a first population of a cyclosporine or a nanoparticulate cyclosporine, and at least one subsequent component or formulation comprising a subsequent population of cyclosporine or a nanoparticulate cyclosporine. The ingredient-containing particles of the subsequent component further comprises a modified release constituent comprising a release coating or release matrix material, or both. Following oral delivery, the composition in operation delivers a cyclosporine or a nanoparticulate cyclosporine, in a pulsatile or zero order manner.

The present invention utilizes controlled release delivery of cyclosporine or a nanoparticulate cyclosporine, from a solid oral dosage formulation to allow dosage less frequently than before, and preferably once-a-day administration, increasing patient convenience and compliance. The mechanism of controlled release would preferably utilize, but not be limited to, an erodable formulation, a diffusion controlled formulation and an osmotic controlled formulation. A portion of the total dose may be released immediately to allow for rapid onset of effect. The invention would be useful in improving compliance and, therefore, therapeutic outcome for all treatments requiring a cyclosporine or a nanoparticulate cyclosporine, including but not limited to, the prevention and treatment of organ transplant rejection and autoimmune diseases such as psoriasis, rheumatoid arthritis, and other related diseases. This approach would replace conventional cyclosporine tablets and solution, which are administered two times a day as adjunctive therapy in the prevention and treatment of organ transplant rejection and autoimmune diseases such as psoriasis, rheumatoid arthritis, and other related diseases.

The present invention also relates to a controlled modified release composition for the controlled release of a cyclosporine or a nanoparticulate cyclosporine. In particular, the present invention relates to a controlled release composition that in operation a cyclosporine or a nanoparticulate cyclosporine, in a pulsatile or zero order manner, preferably during a period of up to twenty-four hours. The present invention further relates to solid oral dosage forms containing a controlled release composition.

Preferred controlled release formulations are erodable formulations, diffusion controlled formulations and osmotic controlled formulations. According to the invention, a portion of the total dose may be released immediately to allow for rapid onset of effect, with the remaining portion of the total dose released over an extended time period. The invention would be useful in improving compliance and, therefore, therapeutic outcome for all treatments requiring a cyclosporine or a nanoparticulate cyclosporine including but not limited to, prevention and treatment of organ transplant rejection and autoimmune diseases such as psoriasis, rheumatoid arthritis, and other related diseases.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

I. Nanoparticulate Cyclosporine Compositions

The present invention is directed to a nanoparticulate composition comprising a cyclosporine. The composition comprises a cyclosporine and preferably at least one surface stabilizer adsorbed on the surface of the drug. The cyclosporine particles have an effective average particle size of less than about 2000 nm in diameter. By "effective average particle size" of less than a specified amount, it is meant that at least 50% of the particles have a particle size of less than about that amount.

As taught by the '684 patent, and as exemplified in the examples below, not every combination of surface stabilizer and active agent will result in a stable nanoparticulate composition. It was surprisingly discovered that stable, nanoparticulate cyclosporine formulations can be made.

Advantages of the nanoparticulate cyclosporine formulation of the invention include, but are not limited to: (1) smaller tablet or other solid dosage form size; (2) smaller doses of drug required to obtain the same pharmacological effect as compared to conventional microcrystalline forms of cyclosporine; (3) increased bioavailability as compared to conventional microcrystalline forms of cyclosporine; (4) improved pharmacokinetic profiles; (5) an increased rate of dissolution for the cyclosporine compositions as compared to conventional microcrystalline forms of the same cyclosporine; and (6) the cyclosporine compositions can be used in conjunction with other active agents useful in the prevention and treatment of organ transplant rejection and autoimmune diseases such as psoriasis, rheumatoid arthritis, and other related diseases.

The present invention also includes a nanoparticulate cyclosporine composition together with one or more non-toxic physiologically acceptable carriers, adjuvants, or vehicles, collectively referred to as carriers. The compositions can be formulated for parental injection (e.g., intravenous, intramuscular, or subcutaneous), oral administration in solid, liquid, or aerosol form, vaginal, nasal, rectal, ocular, local (powders, ointments, or drops), buccal, intracisternal, intraperitoneal, or topical administrations, and the like.

A preferred dosage form of the invention is a solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof. A solid dose tablet formulation is preferred.

A. Preferred Characteristics of the Nanoparticulate Cyclosporine Compositions of the Invention 1. Increased Bioavailability The nanoparticulate cyclosporine formulation of the invention is proposed to exhibit increased bioavailability, and require smaller doses as compared to prior conventional cyclosporine formulations.

2. Dissolution Profiles of the Cyclosporine Composition of the Invention

The nanoparticulate cyclosporine composition of the invention is proposed to have an unexpectedly dramatic dissolution profile. Rapid dissolution of an administered active agent is preferable, as faster dissolution generally leads to faster onset of action and greater bioavailability. To improve the dissolution profile and bioavailability of the cyclosporine it would be useful to increase the drug's dissolution so that it could attain a level close to 100%.

The cyclosporine composition of the invention preferably have a dissolution profile in which within about 5 minutes at least about 20% of the composition is dissolved. In other embodiments of the invention, at least about 30% or about 40% of the cyclosporine composition is dissolved within about 5 minutes. In yet other embodiments of the invention, preferably at least 40%, about 50%, about 60%, about 70%, or about 80% of the cyclosporine composition is dissolved within about 10 minutes. Finally, in another embodiment of the invention, preferably at least about 70%, about 80%, about 90%, or about 100% of the cyclosporine composition is dissolved within 20 minutes.

Dissolution is preferably measured in a medium which is discriminating. Such a dissolution medium will produce two very different dissolution curves for two products having very different dissolution profiles in gastric juices; i.e., the dissolution medium is predictive of in vivo dissolution of a composition. An exemplary dissolution medium is an aqueous medium containing the surfactant sodium lauryl sulfate at 0.025 M. Determination of the amount dissolved can be carried out by spectrophotometry. The rotating blade method (European Pharmacopoeia) can be used to measure dissolution.

3. Redispersability of the Cyclosporine Compositions of the Invention

An additional feature of the cyclosporine composition of the invention is that the composition redisperses such that the effective average particle size of the redispersed cyclosporine particles is less than about 2 microns in diameter. This is significant, as if upon administration the cyclosporine compositions of the invention did not redisperse to a substantially nanoparticulate size, then the dosage form may lose the benefits afforded by formulating the cyclosporine into a nanoparticulate size.

This is because nanoparticulate active agent compositions benefit from the small particle size of the active agent; if the active agent does not disperse into the small particle sizes upon administration, them "clumps" or agglomerated active agent particles are formed, owing to the extremely high surface free energy of the nanoparticulate system and the thermodynamic driving force to achieve an overall reduction in free energy. With the formulation of such agglomerated particles, the bioavailability of the dosage form my fall well below that observed with the liquid dispersion form of the nanoparticulate active agent.

In other embodiments of the invention, the redispersed cyclosporine particles of the invention have an effective average particle size of less than about less than about 1900 nm in diameter, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

4. Cyclosporine Used in Conjunction with Other Active Agents

The cyclosporine composition of the invention can additionally comprise one or more compounds useful in the prevention and treatment of organ transplant rejection and autoimmune diseases such as psoriasis, rheumatoid arthritis, and other related diseases, or the cyclosporine composition can be administered in conjunction with such a compound. Examples of such compounds include, but are not limited to corticosteroids, anthralin, calcipotriene, coal tar, siaclic acid, steroids, tazarotene, methotrexate, oral retinoids, non-steroidal anti-inflammatory drugs, azulfidine, corticosteroids, gold, and hydroxychoroquine.

B. Nanoparticulate Cyclosporine Composition

The invention provides a composition comprising cyclosporine particles and at least one surface stabilizer. The surface stabilizers preferably are adsorbed on, or associated with, the surface of the cyclosporine particles. Surface stabilizers especially useful herein preferably physically adhere on, or associate with, the surface of the nanoparticulate cyclosporine particles, but do not chemically react with the cyclosporine particles or itself. Individually adsorbed molecules of the surface stabilizer are essentially free of intermolecular cross-linkages.

The present invention also includes a cyclosporine composition together with one or more non-toxic physiologically acceptable carriers, adjuvants, or vehicles, collectively referred to as carriers. The composition can be formulated for parenteral injection (e.g., intravenous, intramuscular, or subcutaneous), oral administration in solid, liquid, or aerosol form, vaginal, nasal, rectal, ocular, local (powders, ointments or drops), buccal, intracistemal, intraperitoneal, or topical administration, and the like.

1. Surface Stabilizers

The choice of a surface stabilizer for a cyclosporine is non-trivial and required extensive experimentation to realize a desirable formulation. Accordingly, the present invention is directed to the surprising discovery that nanoparticulate cyclosporine compositions can be made.

Combinations of more than one surface stabilizer can be used in the invention. Useful surface stabilizers which can be employed in the invention include, but are not limited to, known organic and inorganic pharmaceutical excipients. Such excipients include various polymers, low molecular weight oligomers, natural products, and surfactants. Surface stabilizers include nonionic, anionic, cationic, ionic, and zwitterionic surfactants.

Representative examples of surface stabilizers include hydroxypropyl methylcellulose (now known as hypromellose), hydroxypropylcellulose, polyvinylpyrrolidone, sodium lauryl sulfate, dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hypromellose phthalate, noncrystalline cellulose, magnesium aluminium silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-1OG® or Surfactant 10-G® (Olin Chemicals, Stamford, Conn.); Crodestas SL-40® (Croda, Inc.); and SA9OHCO, which is $C_{18}H_{37}CH_2(CON(CH_3)$—$CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate, and the like.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$-dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly[diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Nonpolymeric surface stabilizers are any nonpolymeric compound, such benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$:

(i) none of $R_1$-$R_4$ are $CH_3$;
(ii) one of $R_1$-$R_4$ is $CH_3$;
(iii) three of $R_1$-$R_4$ are $CH_3$;
(iv) all of $R_1$-$R_4$ are $CH_3$;
(v) two of $R_1$-$R_4$ are $CH_3$, one of $R_1$-$R_4$ is $C_6H_5CH_2$, and one of $R_1$-$R_4$ is an alkyl chain of seven carbon atoms or less;
(vi) two of $R_1$-$R_4$ are $CH_3$, one of $R_1$-$R_4$ is $C_6H_5CH_2$, and one of $R_1$-$R_4$ is an alkyl chain of nineteen carbon atoms or more;
(vii) two of $R_1$-$R_4$ are $CH_3$ and one of $R_1$-$R_4$ is the group $C_6H_5(CH_2)_n$, where n>1;
(viii) two of $R_1$-$R_4$ are $CH_3$, one of $R_1$-$R_4$ is $C_6H_5CH_2$, and one of $R_1$-$R_4$ comprises at least one heteroatom;
(ix) two of $R_1$-$R_4$ are $CH_3$, one of $R_1$-$R_4$ is $C_6H_5CH_2$, and one of $R_1$-$R_4$ comprises at least one halogen;
(x) two of $R_1$-$R_4$ are $CH_3$, one of $R_1$-$R_4$ is $C_6H_5CH_2$, and one of $R_1$-$R_4$ comprises at least one cyclic fragment;
(xi) two of $R_1$-$R_4$ are $CH_3$ and one of $R_1$-$R_4$ is a phenyl ring; or
(xii) two of $R_1$-$R_4$ are $CH_3$ and two of $R_1$-$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The surface stabilizers are commercially available and/or can be prepared by techniques known in the art. Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference.

2. Other Pharmaceutical Excipients

The pharmaceutical composition according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™).

Suitable lubricants, including agents that act on the flowability of the powder to be compressed, are colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH1101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

3. Nanoparticulate Cyclosporine Particle Size

The compositions of the invention contain nanoparticulate cyclosporine particles which have an effective average particle size of less than about 2000 nm (i.e., 2 microns) in diameter, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

By "an effective average particle size of less than" a specified amount, it is meant that at least 50% of the cyclosporine particles have a particle size of less than about 2000 nm in diameter, 1900 nm, 1800 nm, etc., when measured by the above-noted techniques. Preferably, at least about 70%, about 90%, or about 95% of the cyclosporine particles have a particle size of less than the effective average, i.e., less than about 2000 nm in diameter, 1900 nm, 1800 nm, 1700 nm, etc.

In the present invention, the value for D50 of a nanoparticulate cyclosporine composition is the particle size below which 50% of the cyclosporine particles fall, by weight. Similarly, D90 is the particle size below which 90% of the cyclosporine particles fall, by weight.

4. Concentration of Cyclosporine and Surface Stabilizers

The relative amounts of cyclosporine and one or more surface stabilizers can vary widely. The optimal amount of the individual components can depend, for example, upon the particular cyclosporine selected, the hydrophilic lipophilic balance (HLB), melting point, and the surface tension of water solutions of the stabilizer, etc.

The concentration of the cyclosporine can vary from about 99.5% to about 0.001%, from about 95% to about 0.1%, or from about 90% to about 0.5%, by weight, based on the total combined weight of the cyclosporine and at least one surface stabilizer, not including other excipients.

The concentration of the at least one surface stabilizer can vary from about 0.5% to about 99.999%, from about 5.0% to about 99.9%, or from about 10% to about 99.5%, by weight, based on the total combined dry weight of the cyclosporine and at least one surface stabilizer, not including other excipients.

5. Exemplary Nanoparticulate Cyclosporine Tablet Formulations

Several exemplary cyclosporine tablet formulations are given below. These examples are not intended to limit the claims in any respect, but rather to provide exemplary tablet formulations of cyclosporine which can be utilized in the methods of the invention. Such exemplary tablets can also comprise a coating agent.

| Exemplary Nanoparticulate Cyclosporine Tablet Formulation #1 | |
|---|---|
| Component | g/Kg |
| Cyclosporine | about 50 to about 500 |
| Hypromellose, USP | about 10 to about 70 |
| Docusate Sodium, USP | about 1 to about 10 |
| Sucrose, NF | about 100 to about 500 |
| Sodium Lauryl Sulfate, NF | about 1 to about 40 |
| Lactose Monohydrate, NF | about 50 to about 400 |
| Silicified Microcrystalline Cellulose | about 50 to about 300 |
| Crospovidone, NF | about 20 to about 300 |
| Magnesium Stearate, NF | about 0.5 to about 5 |

| Exemplary Nanoparticulate Cyclosporine Tablet Formulation #2 | |
|---|---|
| Component | g/Kg |
| Cyclosporine | about 100 to about 300 |
| Hypromellose, USP | about 30 to about 50 |
| Docusate Sodium, USP | about 0.5 to about 10 |
| Sucrose, NF | about 100 to about 300 |
| Sodium Lauryl Sulfate, NF | about 1 to about 30 |
| Lactose Monohydrate, NF | about 100 to about 300 |
| Silicified Microcrystalline Cellulose | about 50 to about 200 |
| Crospovidone, NF | about 50 to about 200 |
| Magnesium Stearate, NF | about 0.5 to about 5 |

| Exemplary Nanoparticulate Cyclosporine Tablet Formulation #3 | |
|---|---|
| Component | g/Kg |
| Cyclosporine | about 200 to about 225 |
| Hypromellose, USP | about 42 to about 46 |
| Docusate Sodium, USP | about 2 to about 6 |
| Sucrose, NF | about 200 to about 225 |
| Sodium Lauryl Sulfate, NF | about 12 to about 18 |
| Lactose Monohydrate, NF | about 200 to about 205 |
| Silicified Microcrystalline Cellulose | about 130 to about 135 |
| Crospovidone, NF | about 112 to about 118 |
| Magnesium Stearate, NF | about 0.5 to about 3 |

| Exemplary Nanoparticulate Cyclosporine Tablet Formulation #4 | |
|---|---|
| Component | g/Kg |
| Cyclosporine | about 119 to about 224 |
| Hypromellose, USP | about 42 to about 46 |
| Docusate Sodium, USP | about 2 to about 6 |
| Sucrose, NF | about 119 to about 224 |
| Sodium Lauryl Sulfate, NF | about 12 to about 18 |
| Lactose Monohydrate, NF | about 119 to about 224 |
| Silicified Microcrystalline Cellulose | about 129 to about 134 |
| Crospovidone, NF | about 112 to about 118 |
| Magnesium Stearate, NF | about 0.5 to about 3 |

C. Methods of Making Nanoparticulate Cyclosporine Compositions

The nanoparticulate cyclosporine composition can be made using, for example, milling, homogenization, precipitation, freezing, or template emulsion techniques. Exemplary methods of making nanoparticulate compositions are described in the '684 patent. Methods of making Methods of making nanoparticulate compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference.

The resultant nanoparticulate cyclosporine composition or dispersion can be utilized in solid or liquid dosage formulations, such as liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc.

1. Milling to Obtain a Nanoparticulate Cyclosporine Dispersions

Milling a cyclosporine to obtain a nanoparticulate dispersion comprises dispersing the cyclosporine particles in a liquid dispersion medium in which the cyclosporine is poorly soluble, followed by applying mechanical means in the presence of grinding media to reduce the particle size of the cyclosporine to the desired effective average particle size. The dispersion medium can be, for example, water, safflower oil, ethanol, t-butanol, glycerin, polyethylene glycol (PEG), hexane, or glycol. A preferred dispersion medium is water.

The cyclosporine particles can be reduced in size in the presence of at least one surface stabilizer. Alternatively, cyclosporine particles can be contacted with one or more surface stabilizers after attrition. Other compounds, such as a diluent, can be added to the cyclosporine/surface stabilizer composition during the size reduction process. A dispersion can be manufactured continuously or in a batch mode.

2. Precipitation to Obtain a Nanoparticulate Cyclosporine Composition

Another method of forming the desired nanoparticulate cyclosporine composition is by microprecipitation. This is a method of preparing stable dispersions of poorly soluble active agents in the presence of one or more surface stabilizers and one or more colloid stability enhancing surface active agents free of any trace toxic solvents or solubilized heavy metal impurities. Such a method comprises, for example: (1) dissolving the cyclosporine in a suitable solvent; (2) adding the formulation from step (1) to a solution comprising at least one surface stabilizer; and (3) precipitating the formulation from step (2) using an appropriate non-solvent. The method can be followed by removal of any formed salt, if present, by dialysis or diafiltration and concentration of the dispersion by conventional means.

3. Homogenization to Obtain Nanoparticulate Cyclosporine Compositions

Exemplary homogenization methods of preparing active agent nanoparticulate compositions are described in U.S. Pat. No. 5,510,118, for "Process of Preparing Therapeutic Compositions Containing Nanoparticles." Such a method comprises dispersing particles of a cyclosporine in a liquid dispersion medium, followed by subjecting the dispersion to homogenization to reduce the particle size of a cyclosporine to the desired effective average particle size. The cyclosporine particles can be reduced in size in the presence of at least one surface stabilizer. Alternatively, the cyclosporine particles can be contacted with one or more surface stabilizers either before or after attrition. Other compounds, such as a diluent, can be added to the cyclosporine/surface stabilizer composition either before, during, or after the size reduction process. Dispersions can be manufactured continuously or in a batch mode.

4. Cryogenic Methodologies to Obtain Nanoparticulate Cyclosporine Compositions

Another method of forming the desired nanoparticulate cyclosporine composition is by spray freezing into liquid (SFL). This technology comprises an organic or organoaqueous solution of cyclosporine with stabilizers, which is injected into a cryogenic liquid, such as liquid nitrogen. The droplets of the cyclosporine solution freeze at a rate sufficient to minimize crystallization and particle growth, thus formulating nanostructured cyclosporine particles. Depending on the choice of solvent system and processing conditions, the nanoparticulate cyclosporine particles can have varying particle morphology. In the isolation step, the nitrogen and solvent are removed under conditions that avoid agglomeration or ripening of the cyclosporine particles.

As a complementary technology to SFL, ultra rapid freezing (URF) may also be used to created equivalent nanostructured cyclosporine particles with greatly enhanced surface area. URF comprises taking a water-miscible, anhydrous, organic, or organoaqueous solution of PG derivative with stabilizers and applying it onto a cryogenic substrate. The solvent is then removed, by means such as lyophilization or atmospheric freeze-drying with the resulting nanostructured PG derivative remaining.

5. Emulsion Methodologies to Obtain Nanoparticulate Cyclosporine Compositions

Another method of forming the desired nanoparticulate cyclosporine composition is by template emulsion. Template emulsion creates nanostructured cyclosporine particles with controlled particle size distribution and rapid dissolution performance. The method comprises an oil-in-water emulsion that is prepared, then swelled with a non-aqueous solution comprising the cyclosporine and stabilizers. The particle size distribution of the cyclosporine particles is a direct result of the size of the emulsion droplets prior to loading with the cyclosporine a property which can be controlled and optimized in this process. Furthermore, through selected use of solvents and stabilizers, emulsion stability is achieved with no or suppressed Ostwald ripening. Subsequently, the solvent and water are removed, and the stabilized nanostructured cyclosporine particles are recovered. Various cyclosporine particles morphologies can be achieved by appropriate control of processing conditions.

D. Methods of Using the Nanoparticulate Cyclosporine Compositions of the Invention The invention provides a method of increasing bioavailability of a cyclosporine in a subject. Such a method comprises orally administering to a subject an effective amount of a composition comprising a cyclosporine. The cyclosporine composition, in accordance with standard pharmacokinetic practice, has a bioavailability that is about 50% greater than a conventional dosage form, about 40% greater, about 30% greater, about 20% or about 10% greater.

The composition of the invention are useful in the prevention and treatment of organ transplant rejection and autoimmune diseases such as psoriasis, rheumatoid arthritis, and other related diseases.

The cyclosporine compounds of the invention can be administered to a subject via any conventional means including, but not limited to, orally, rectally, ocularly, parenterally (e.g., intravenous, intramuscular, or subcutaneous), intracisternally, pulmonary, intravaginally, intraperitoneally, locally (e.g., powders, ointments or drops), or as a buccal or nasal spray. As used herein, the term "subject" is used to mean an animal, preferably a mammal, including a human or non-human. The terms patient and subject may be used interchangeably.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate cyclosporine compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include, but are not limited to, capsules, tablets, pills, powders, and granules. In such solid dosage forms, the active agent is admixed with at least one of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to a cyclosporine, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

'Therapeutically effective amount' as used herein with respect to a cyclosporine, dosage shall mean that dosage that provides the specific pharmacological response for which a cyclosporine is administered in a significant number of subjects in need of such treatment. It is emphasized that 'therapeutically effective amount,' administered to a particular subject in a particular instance will not always be effective in treating the diseases described herein, even though such dosage is deemed a 'therapeutically effective amount' by those skilled in the art. It is to be further understood that cyclosporine dosages are, in particular instances, measured as oral dosages, or with reference to drug levels as measured in blood.

One of ordinary skill will appreciate that effective amounts of a cyclosporine can be determined empirically and can be employed in pure form or, where such forms exist, in pharmaceutically acceptable salt, ester, or prodrug form. Actual dosage levels of a cyclosporine in the nanoparticulate compositions of the invention may be varied to obtain an amount of a cyclosporine that is effective to obtain a desired therapeutic response for a particular composition and method of administration. The selected dosage level therefore depends upon the desired therapeutic effect, the route of administration, the potency of the administered cyclosporine, the desired duration of treatment, and other factors.

Dosage unit compositions may contain such amounts of such submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

II. Controlled Release Cyclosporine Compositions

Controlled release compositions comprising cyclosporine are described. Controlled release compositions comprising nanoparticulate cyclosporine are also described.

A. Multiparticulate Controlled Release Cyclosporine Compositions

The above objects are realized by a controlled release composition having a first component comprising a first population of a cyclosporine or a nanoparticulate cyclosporine, and a subsequent component comprising a subsequent population of cyclosporine or nanoparticulate cyclosporine. The ingredient-containing particles of the subsequent component are coated with a modified release coating. Alternatively or additionally, the subsequent population of cyclosporine or nanoparticulate cyclosporine containing particles further comprises a modified release matrix material. Following oral delivery, the composition in operation delivers the cyclosporine in a pulsatile or zero order manner.

In a preferred embodiment, the controlled release composition of the present invention comprises a first component which is an immediate release component.

The modified release coating applied to the subsequent population of a cyclosporine or a nanoparticulate cyclosporine causes a lag time between the release of active from the first population of active cyclosporine-containing particles and the release of active from the subsequent population of active cyclosporine-containing particles. Similarly, the presence of a modified release matrix material in the subsequent population of active cyclosporine-containing particles causes a lag time between the release of cyclosporine from the first population of cyclosporine-containing particles and the release of active ingredient from the subsequent population of active ingredient containing particles. The duration of the lag time may be varied by altering the composition and/or the amount of the modified release coating and/or altering the composition and/or amount of modified release matrix material utilized. Thus, the duration of the lag time can be designed to mimic a desired plasma profile.

Because the plasma profile produced by the controlled release composition upon administration is substantially similar to the plasma profile produced by the administration of two or more IR dosage forms given sequentially, the controlled release composition of the present invention is particularly useful for administering a cyclosporine or a nanoparticulate cyclosporine for which patient tolerance may be problematical. This controlled release composition is therefore advantageous for reducing or minimizing the development of patient tolerance to the active ingredient in the composition.

In a preferred embodiment of the present invention, cyclosporine or a nanoparticulate cyclosporine and the composition in operation delivers the cyclosporine in a bimodal or pulsatile or zero order manner. Such a composition in operation produces a plasma profile which substantially mimics that obtained by the sequential administration of two IR doses as, for instance, in a typical treatment regimen.

The present invention further relates to a controlled release composition comprising a cyclosporine or a nanoparticulate cyclosporine which in operation produced a plasma profile that eliminates the "peaks" and "troughs" produced by the administration of two or more IR dosage forms given sequentially if such a profile is beneficial. This type of profile can be obtained using a controlled release mechanism that allows for "zero-order" delivery.

The present invention also provides solid oral dosage forms comprising a composition according to the invention.

The term "particulate" as used herein refers to a state of matter which is characterized by the presence of discrete particles, pellets, beads or granules irrespective of their size, shape or morphology. The term "multiparticulate" as used herein means a plurality of discrete or aggregated particles, pellets, beads, granules or mixture thereof, irrespective of their size, shape or morphology.

The term "modified release" as used herein with respect to the coating or coating material or used in any other context, means release which is not immediate release and is taken to encompass controlled release, sustained release and delayed release.

The term "time delay" as used herein refers to the duration of time between administration of the composition and the release of the cyclosporine from a particular component.

The term "lag time" as used herein refers to the time between delivery of the cyclosporine from one component and the subsequent delivery cyclosporine from another component.

The term "erodable" as used herein refers to formulations which may be worn away, diminished, or deteriorated by the action of substances within the body.

The term "diffusion controlled" as used herein refers to formulations which may spread as the result of their spontaneous movement, for example, from a region of higher to one of lower concentration.

The term "osmotic controlled" as used herein refers to formulations which may spread as the result of their movement through a semipermeable membrane into a solution of higher concentration that tends to equalize the concentrations of the formulation on the two sides of the membrane.

The active ingredient in each component may be the same or different. For example, a composition may comprise a first component containing cyclosporine, and the subsequent component may comprise a second active ingredient which would be desirable for combination therapies. Indeed, two or more active ingredients may be incorporated into the same component when the active ingredients are compatible with each other. A drug compound present in one component of the composition may be accompanied by, for example, an enhancer compound or a sensitizer compound in another component of the composition, in order to modify the bioavailability or therapeutic effect of the drug compound.

As used herein, the term "enhancer" refers to a compound which is capable of enhancing the absorption and/or bioavailability of an active ingredient by promoting net transport across the GIT in an animal, such as a human. Enhancers include but are not limited to medium chain fatty acids; salts, esters, ethers and derivatives thereof, including glycerides and triglycerides; non-ionic surfactants such as those that can be prepared by reacting ethylene oxide with a fatty acid, a fatty alcohol, an alkylphenol or a sorbitan or glycerol fatty acid ester; cytochrome P450 inhibitors, P-glycoprotein inhibitors and the like; and mixtures of two or more of these agents.

The amount of the active ingredient contained in the composition and in dosage forms made therefrom may be allocated evenly or unevenly across the different particle populations comprising the components of the composition and contained in the dosage forms made therefrom. In one embodiment, the active ingredient contained in the particles of the first component comprises a minor portion of the total amount of active ingredient in the composition or dosage form, and the amount of the active ingredient in the other components comprises a major portion of the total amount of active ingredient in the composition or dosage form. In one such embodiment comprising two components, about 20% of the total amount of the active ingredient is contained in the particles of the first component, and about 80% of the total amount of the active ingredient is contained in the particles of the second component.

The proportion of the cyclosporine or the nanoparticulate cyclosporine contained in each component may be the same or different depending on the desired dosing regime. The cyclosporine is present in the first component and in the second component in any amount sufficient to elicit a therapeutic response. The cyclosporine, when applicable, may be present either in the form of one substantially optically pure enantiomer or as a mixture, racemic or otherwise, of enantiomers. The cyclosporine is preferably present in a composition in an amount of from 0.1-500 mg, preferably in the amount of from 1-100 mg. The cyclosporine is preferably present in the first component in an amount of from 0.5-60 mg; more preferably the cyclosporine, is present in the first component in an amount of from 2.5-30 mg. The cyclosporine is present in the subsequent components in an amount within a similar range to that described for the first component.

The time release characteristics for the delivery of the cyclosporine or the nanoparticulate cyclosporine from each of the components may be varied by modifying the composition of each component, including modifying any of the excipients or coatings which may be present. In particular, the release of the cyclosporine may be controlled by changing the composition and/or the amount of the modified release coating on the particles, if such a coating is present. If more than one modified release component is present, the modified release coating for each of these components may be the same or different. Similarly, when modified release is facilitated by the inclusion of a modified release matrix material, release of the active ingredient may be controlled by the choice and amount of modified release matrix material utilized. The modified release coating may be present, in each component, in any amount that is sufficient to yield the desired delay time for each particular component. The modified release coating may be preset, in each component, in any amount that is sufficient to yield the desired time lag between components.

The lag time or delay time for the release of the cyclosporine or the nanoparticulate cyclosporine from each component may also be varied by modifying the composition of each of the components, including modifying any excipients and coatings which may be present. For example, the first component may be an immediate release component wherein the cyclosporine is released immediately upon administration. Alternatively, the first component may be, for example, a time-delayed immediate release component in which the cyclosporine is released substantially in its entirety immediately after a time delay. The subsequent component may be, for example, a time-delayed immediate release component as just described or, alternatively, a time-delayed sustained release or extended release component in which the cyclosporine is released in a controlled fashion over an extended period of time.

As will be appreciated by those skilled in the art, the exact nature of the plasma concentration curve will be influenced by the combination of all of these factors just described. In particular, the lag time between the delivery (and thus also the on-set of action) of the cyclosporine in each component may be controlled by varying the composition and coating (if present) of each of the components. Thus by variation of the composition of each component (including the amount and nature of the active ingredient(s)) and by variation of the lag time, numerous release and plasma profiles may be obtained. Depending on the duration of the lag time between the release of the cyclosporine from each component and the nature of the release of the cyclosporine from each component (i.e. immediate release, sustained release etc.), the pulses in the plasma profile may be well separated and clearly defined peaks (e.g. when the lag time is long) or the pulses may be superimposed to a degree (e.g. in when the lag time is short).

In a preferred embodiment, the controlled release composition according to the present invention has an immediate release component and at least one modified release component, the immediate release component comprising a first population of active ingredient containing particles and the modified release components comprising subsequent populations of active ingredient containing particles. The subsequent modified release components may comprise a controlled release coating. Additionally or alternatively, the subsequent modified release components may comprise a modified release matrix material. In operation, administration of such a multi-particulate modified release composition having, for example, a single modified release component results in characteristic pulsatile plasma concentration levels of the cyclosporine or the nanoparticulate cyclosporine in which the immediate release component of the composition gives rise to a first peak in the plasma profile and the modified release component gives rise to a second peak in the plasma profile. Embodiments of the invention comprising more than one modified release component give rise to further peaks in the plasma profile.

Such a plasma profile produced from the administration of a single dosage unit is advantageous when it is desirable to deliver two (or more) pulses of active ingredient without the need for administration of two (or more) dosage units. Additionally, in the case of treating organ transplant rejection and autoimmune diseases, it is particularly useful to have such a bimodal plasma profile. For example, a typical cyclosporine treatment regime consists of administration of two doses of an immediate release dosage formulation given four hours apart. This type of regime has been found to be therapeutically effective and is widely used. As previously mentioned, the development of patient tolerance is an adverse effect sometimes associated with cyclosporine treatments. It is believed that the trough in the plasma profile between the two peak plasma concentrations is advantageous in reducing the development of patient tolerance by providing a period of wash out of the cyclosporine.

In addition, a delivery system having a zero order or pseudo zero order delivery that eliminates or minimizes the "peak" to "trough" ratio is also described.

Any coating material which modifies the release of the cyclosporine or the nanoparticulate cyclosporine in the desired manner may be used. In particular, coating materials suitable for use in the practice of the invention include but are not limited to polymer coating materials, such as cellulose acetate phthalate, cellulose acetate trimaletate, hydroxy propyl methylcellulose phthalate, polyvinyl acetate phthalate, ammonio methacrylate copolymers such as those sold under the Trade Mark Eudragit® RS and RL, poly acrylic acid and poly acrylate and methacrylate copolymers such as those sold under the Trade Mark Eudragit S and L, polyvinyl acetaldiethylamino acetate, hydroxypropyl methylcellulose acetate succinate, shellac; hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, gelatin, starch, and cellulose based cross-linked polymers—in which the degree of crosslinking is low so as to facilitate adsorption of water and expansion of the polymer matrix, hydroxypropyl cellulose, hydroxypropyl methylcellulose, polyvinylpyrrolidone, crosslinked starch, microcrystalline cellulose, chitin, aminoacryl-methacrylate copolymer (Eudragit® RS-PM, Rohm & Haas), pullulan, collagen, casein, agar, gum arabic, sodium carboxymethyl cellulose, (swellable hydrophilic polymers) poly(hydroxyalkyl methacrylate) (m. wt. .about.5 k-5,000 k), polyvinylpyrrolidone (m. wt. .about.10 k-360 k), anionic and cationic hydrogels, polyvinyl alcohol having a low acetate residual, a swellable mixture of agar and carboxymethyl cellulose, copolymers of maleic anhydride and styrene, ethylene, propylene or isobutylene, pectin (m. wt. .about.30 k-300 k), polysaccharides such as agar, acacia, karaya, tragacanth, algins and guar, polyacrylamides, Polyox® polyethylene oxides (m. wt. .about.100 k-5,000 k), AquaKeep® acrylate polymers, diesters of polyglucan, crosslinked polyvinyl alcohol and poly N-vinyl-2-pyrrolidone, sodium starch glucolate (e.g. Explotab®; Edward Mandell C. Ltd.); hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, polyethylene oxides (e.g. Polyox®, Union Carbide), methyl ethyl cellulose, ethylhydroxy ethylcellulose, cellulose acetate, cellulose butyrate, cellulose propionate, gelatin, collagen, starch, maltodextrin, pullulan, polyvinyl pyrrolidone, polyvinyl alcohol, polyvinyl acetate, glycerol fatty acid esters, polyacrylamide, polyacrylic acid, copolymers of methacrylic acid or methacrylic acid (e.g. Eudragit®, Rohm and Haas), other acrylic acid derivatives, sorbitan esters, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures and blends thereof. As will be appreciated by the person skilled in the art, excipients such as plasticisers, lubricants, solvents and the like may be added to the coating. Suitable plasticisers include for example acetylated monoglycerides; butyl phthalyl butyl glycolate; dibutyl tartrate; diethyl phthalate; dimethyl phthalate; ethyl phthalyl ethyl glycolate; glycerin; propylene glycol; triacetin; citrate; tripropioin; diacetin; dibutyl phthalate; acetyl monoglyceride; polyethylene glycols; castor oil; triethyl citrate; polyhydric alcohols, glycerol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate.

When the modified release component comprises a modified release matrix material, any suitable modified release matrix material or suitable combination of modified release matrix materials may be used. Such materials are known to those skilled in the art. The term "modified release matrix material" as used herein includes hydrophilic polymers, hydrophobic polymers and mixtures thereof which are capable of modifying the release of a cyclosporine or a nanoparticulate cyclosporine dispersed therein in vitro or in vivo. Modified release matrix materials suitable for the practice of the present invention include but are not limited to microcrytalline cellulose, sodium carboxymethylcellulose, hydroxyalkylcelluloses such as hydroxypropylmethylcellulose and hydroxypropylcellulose, polyethylene oxide, alkylcelluloses such as methylcellulose and ethylcellulose, polyethylene glycol, polyvinylpyrrolidone, cellulose acteate, cellulose acetate butyrate, cellulose acteate phthalate, cellulose acteate trimellitate, polyvinylacetate phthalate, polyalkylmethacrylates, polyvinyl acetate and mixture thereof.

A controlled release composition according to the present invention may be incorporated into any suitable dosage form which facilitates release of the active ingredient in a pulsatile or zero order manner. Typically, the dosage form may be a blend of the different populations of cyclosporine-containing particles which make up the immediate release and the modified release components, the blend being filled into suitable capsules, such as hard or soft gelatin capsules. Alternatively, the different individual populations of active ingredient containing particles may be compressed (optionally with additional excipients) into mini-tablets which may be subsequently filled into capsules in the appropriate proportions. Another suitable dosage form is that of a multilayer tablet. In this instance the first component of the controlled release composition may be compressed into one layer, with the second component being subsequently added as a second layer of the multilayer tablet. The populations of cyclosporine-containing particles making up the composition of the invention may further be included in rapidly dissolving dosage forms such as an effervescent dosage form or a fast-melt dosage form.

The composition according to the invention comprises at least two populations of cyclosporine-containing particles which have different in vitro dissolution profiles.

Preferably, in operation the composition of the invention and the solid oral dosage forms containing the composition release the cyclosporine or the nanoparticulate cyclosporine such that substantially all of the cyclosporine contained in the first component is released prior to release of the cyclosporine from the second component. When the first component comprises an IR component, for example, it is preferable that release of the cyclosporine from the second component is delayed until substantially all the cyclosporine in the IR component has been released. Release of the cyclosporine from the second component may be delayed as detailed above by the use of a modified release coating and/or a modified release matrix material.

More preferably, when it is desirable to minimize patient tolerance by providing a dosage regime which facilitates wash-out of a first dose of the cyclosporine or the nanoparticulate cyclosporine from a patient's system, release of the cyclosporine from the second component is delayed until substantially all of the cyclosporine contained in the first component has been released, and further delayed until at least a portion the cyclosporine released from the first component has been cleared from the patient's system. In a preferred embodiment, release of the cyclosporine from the second component of the composition in operation is substantially, if not completely, delayed for a period of at least about two hours after administration of the composition.

The cyclosporine release of the drug from the second component of the composition in operation is substantially, if not completely, delayed for a period of at least about four hours, preferably about four hours, after administration of the composition.

B. Other Delivery Mechanisms for Controlled Release Cyclosporine Compositions

As described herein, the invention includes various types of controlled release systems by which the active drug may be delivered in a pulsatile or zero order manner. These systems include, but are not limited to: films with the drug in a polymer matrix (monolithic devices); the drug contained by the polymer (reservoir devices); polymeric colloidal particles or microencapsulates (microparticles, microspheres or nanoparticles) in the form of reservoir and matrix devices; drug contained by a polymer containing a hydrophilic and/or leachable additive eg, a second polymer, surfactant or plasticiser, etc. to give a porous device, or a device in which the drug release may be osmotically 'controlled' (both reservoir and matrix devices); enteric coatings (ionise and dissolve at a suitable pH); (soluble) polymers with (covalently) attached 'pendant' drug molecules; devices where release rate is controlled dynamically: eg, the osmotic pump.

The delivery mechanism of the invention will control the rate of release of the drug. While some mechanisms will release the drug at a constant rate (zero order), others will vary as a function of time depending on factors such as changing concentration gradients or additive leaching leading to porosity, etc.

Polymers used in sustained release coatings are necessarily biocompatible, and ideally biodegradable. Examples of both naturally occurring polymers such as Aquacoat® (FMC Corporation, Food & Pharmaceutical Products Division, Philadelphia, USA) (ethylcellulose mechanically spheronised to sub-micron sized, aqueous based, pseudo-latex dispersions), and also synthetic polymers such as the Eudragit® (Röhm Pharma, Weiterstadt.) range of poly(acrylate, methacrylate) copolymers are known in the art.

1. Reservoir Devices

A typical approach to controlled release is to encapsulate or contain the drug entirely (eg, as a core), within a polymer film or coat (ie, microcapsules or spray/pan coated cores).

The various factors that can affect the diffusion process may readily be applied to reservoir devices (eg, the effects of additives, polymer functionality {and, hence, sink-solution pH} porosity, film casting conditions, etc.) and, hence, the choice of polymer must be an important consideration in the development of reservoir devices. Modeling the release characteristics of reservoir devices (and monolithic devices) in which the transport of the drug is by a solution-diffusion mechanism therefore typically involves a solution to Fick's second law (unsteady-state conditions; concentration dependent flux) for the relevant boundary conditions. When the device contains dissolved active agent, the rate of release decreases exponentially with time as the concentration (activity) of the agent (ie, the driving force for release) within the device decreases (ie, first order release). If, however, the active agent is in a saturated suspension, then the driving force for release is kept constant (zero order) until the device is no longer saturated. Alternatively the release-rate kinetics may be desorption controlled, and a function of the square root of time.

Transport properties of coated tablets, may be enhanced compared to free-polymer films, due to the enclosed nature of the tablet core (permeant) which may enable the internal build-up of an osmotic pressure which will then act to force the permeant out of the tablet.

The effect of deionised water on salt containing tablets coated in poly(ethylene glycol) (PEG)-containing silicone elastomer, and also the effects of water on free films has been investigated. The release of salt from the tablets was found to be a mixture of diffusion through water filled pores, formed by hydration of the coating, and osmotic pumping. KCl transport through films containing just 10% PEG was negligible, despite extensive swelling observed in similar free films, indicating that porosity was necessary for the release of the KCl which then occurred by 'trans-pore diffusion.' Coated salt tablets, shaped as disks, were found to swell in deionised water and change shape to an oblate spheroid as a result of the build-up of internal hydrostatic pressure: the change in shape providing a means to measure the 'force' generated. As might be expected, the osmotic force decreased with increasing levels of PEG content. The lower PEG levels allowed water to be imbibed through the hydrated polymer; whilst the porosity resulting from the coating dissolving at higher levels of PEG content (20 to 40%) allowed the pressure to be relieved by the flow of KCl.

Methods and equations have been developed, which by monitoring (independently) the release of two different salts (eg, KCl and NaCl) allowed the calculation of the relative magnitudes that both osmotic pumping and trans-pore diffusion contributed to the release of salt from the tablet. At low PEG levels, osmotic flow was increased to a greater extent than was trans-pore diffusion due to the generation of only a low pore number density: at a loading of 20%, both mechanisms contributed approximately equally to the release. The build-up of hydrostatic pressure, however, decreased the osmotic inflow, and osmotic pumping. At higher loadings of PEG, the hydrated film was more porous and less resistant to outflow of salt. Hence, although the osmotic pumping increased (compared to the lower loading), trans-pore diffusion was the dominant release mechanism. An osmotic release mechanism has also been reported for microcapsules containing a water soluble core.

2. Monolithic Devices (Matrix Devices)

Monolithic (matrix) devices are possibly the most common of the devices for controlling the release of drugs. This is possibly because they are relatively easy to fabricate, compared to reservoir devices, and there is not the danger of an accidental high dosage that could result from the rupture of the membrane of a reservoir device. In such a device the active agent is present as a dispersion within the polymer matrix, and they are typically formed by the compression of a polymer/drug mixture or by dissolution or melting. The dosage release properties of monolithic devices may be dependent upon the solubility of the drug in the polymer matrix or, in the case of porous matrixes, the solubility in the sink solution within the particle's pore network, and also the tortuosity of the network (to a greater extent than the permeability of the film), dependent on whether the drug is dispersed in the polymer or dissolved in the polymer. For low loadings of drug, (0 to 5% W/V) the drug will be released by a solution-diffusion mechanism (in the absence of pores). At higher loadings (5 to 10% W/V), the release mechanism will be complicated by the presence of cavities formed near the surface of the device as the drug is lost: such cavities fill with fluid from the environment increasing the rate of release of the drug.

It is common to add a plasticiser (eg, a poly(ethylene glycol)), or surfactant, or adjuvant (ie, an ingredient which increases effectiveness), to matrix devices (and reservoir devices) as a means to enhance the permeability (although, in contrast, plasticiser may be fugitive, and simply serve to aid film formation and, hence, decrease permeability—a property normally more desirable in polymer paint coatings). It was noted that the leaching of PEG acted to increase the permeability of (ethyl cellulose) films linearly as a function of PEG loading by increasing the porosity, however, the films retained their barrier properties, not permitting the transport of electrolyte. It was deduced that the enhancement of their permeability was as a result of the effective decrease in thickness caused by the PEG leaching. This was evinced from plots of the cumulative permeant flux per unit area as a function of time and film reciprocal thickness at a PEG loading of 50% W/W: plots showing a linear relationship between the rate of permeation and reciprocal film thickness, as expected for a (Fickian) solution-diffusion type transport mechanism in a homogeneous membrane. Extrapolation of the linear regions of the graphs to the time axis gave positive intercepts on the time axis: the magnitude of which decreased towards zero with decreasing film thickness. These changing lag times were attributed to the occurrence of two diffusional flows during the early stages of the experiment (the flow of the 'drug' and also the flow of the PEG), and also to the more usual lag time during which the concentration of permeant in the film is building-up. Caffeine, when used as a permeant, showed negative lag times. No explanation of this was forthcoming, but it was noted that caffeine exhibited a low partition coefficient in the system, and that this was also a feature of aniline permeation through polyethylene films which showed a similar negative time lag.

The effects of added surfactants on (hydrophobic) matrix devices has been investigated. It was thought that surfactant may increase the drug release rate by three possible mechanisms: (i) increased solubilisation, (ii) improved 'wettability' to the dissolution media, and (iii) pore formation as a result of surfactant leaching. For the system studied (Eudragit® RL 100 and RS 100 plasticised by sorbitol, Flurbiprofen as the drug, and a range of surfactants) it was concluded that improved wetting of the tablet led to only a partial improvement in drug release (implying that the release was diffusion, rather than dissolution, controlled), although the effect was greater for Eudragit® RS than Eudragit® RL, whilst the greatest influence on release was by those surfactants that were more soluble due to the formation of 'disruptions' in the matrix allowing the dissolution medium access to within the matrix. This is of obvious relevance to a study of latex films which might be suitable for pharmaceutical coatings, due to the ease with which a polymer latex may be prepared with surfactant as opposed to surfactant-free. Differences were found between the two polymers—with only the Eudragit® RS showing interactions between the anionic/cationic surfactant and drug. This was ascribed to the differing levels of quaternary ammonium ions on the polymer.

Composite devices consisting of a polymer/drug matrix coated in a polymer containing no drug also exist. Such a device was constructed from aqueous Eudragit® latices, and was found to give zero order release by diffusion of the drug from the core through the shell. Similarly, a polymer core containing the drug has been produced, but coated this with a shell that was eroded by the gastric fluid. The rate of release of the drug was found to be relatively linear (a function of the rate limiting diffusion process through the shell) and inversely proportional to the shell thickness, whereas the release from the core alone was found to decrease with time.

3. Microspheres

Methods for the preparation of hollow microspheres ('microballoons') with the drug dispersed in the sphere's shell, and also highly porous matrix-type microspheres ('microsponges') have been described. The microsponges were prepared by dissolving the drug and polymer in ethanol. On addition to water, the ethanol diffused from the emulsion droplets to leave a highly porous particle.

The hollow microspheres were formed by preparing a solution of ethanol/dichloro-methane containing the drug and polymer. On pouring into water, this formed an emulsion containing the dispersed polymer/drug/solvent particles, by a coacervation-type process, from which the ethanol (a good solvent for the polymer) rapidly diffused precipitating polymer at the surface of the droplet to give a hard-shelled particle enclosing the drug, dissolved in the dichloromethane. At this point, a gas phase of dichloromethane was generated within the particle which, after diffusing through the shell, was observed to bubble to the surface of the aqueous phase. The hollow sphere, at reduced pressure, then filled with water, which could be removed by a period of drying. (No drug was found in the water.) A suggested use of the microspheres was as floating drug delivery devices for use in the stomach.

4. Pendent Devices

A means of attaching a range of drugs such as analgesics and antidepressants, etc., by means of an ester linkage to poly(acrylate) ester latex particles prepared by aqueous emulsion polymerization has been developed. These latices when passed through an ion exchange resin such that the polymer end groups were converted to their strong acid form could 'self-catalyse' the release of the drug by hydrolysis of the ester link.

Drugs have been attached to polymers, and also monomers have been synthesized with a pendent drug attached. The research group have also prepared their own dosage forms in which the drug is bound to a biocompatible polymer by a labile chemical bond eg, polyanhydrides prepared from a substituted anhydride (itself prepared by reacting an acid chloride with the drug: methacryloyl chloride and the sodium salt of methoxy benzoic acid) were used to form a matrix with a second polymer (Eudragit® RL) which released the drug on hydrolysis in gastric fluid. The use of polymeric Schiff bases suitable for use as carriers of pharmaceutical amines has also been described.

5. Enteric Films

Enteric coatings consist of pH sensitive polymers. Typically the polymers are carboxylated and interact (swell) very little with water at low pH, whilst at high pH the polymers ionise causing swelling, or dissolving of the polymer. Coatings can therefore be designed to remain intact in the acidic environment of the stomach (protecting either the drug from this environment or the stomach from the drug), but to dissolve in the more alkaline environment of the intestine.

6. Osmotically Controlled Devices

The osmotic pump is similar to a reservoir device but contains an osmotic agent (eg, the active agent in salt form) which acts to imbibe water from the surrounding medium via a semi-permeable membrane. Such a device, called the 'elementary osmotic pump', has been described. Pressure is generated within the device which forces the active agent out of the device via an orifice (of a size designed to minimise solute diffusion, whilst preventing the build-up of a hydrostatic pressure head which has the effect of decreasing the osmotic pressure and changing the dimensions {volume} of the device). Whilst the internal volume of the device remains constant, and there is an excess of solid (saturated solution) in the device, then the release rate remains constant delivering a volume equal to the volume of solvent uptake.

7. Electrically Stimulated Release Devices

Monolithic devices have been prepared using polyelectrolyte gels which swelled when, for example, an external electrical stimulus was applied, causing a change in pH. The release could be modulated, by the current, giving a pulsatile release profile.

8. Hydrogels

Hydrogels find a use in a number of biomedical applications, in addition to their use in drug matrices (eg, soft contact lenses, and various 'soft' implants, etc.).

C. Methods of Using Controlled Release Cyclosporine Compositions

The present invention further provides a method of treating a patient suffering from organ transplant rejection or autoimmune diseases such as psoriasis, rheumatoid arthritis, and other related diseases utilizing a cyclosporine or a nanoparticulate cyclosporine comprising the administration of a therapeutically effective amount of a solid oral dosage form of a cyclosporine to provide a pulsed or bimodal or zero order delivery of the cyclosporine. Advantages of the present invention include reducing the dosing frequency required by conventional multiple IR dosage regimes while still maintaining the benefits derived from a pulsatile plasma profile or eliminating or minimizing the "peak" to "trough" ratio. This reduced dosing frequency is advantageous in terms of patient compliance to have a formulation which may be administered at reduced frequency. The reduction in dosage frequency made possible by utilizing the present invention would contribute to reducing health care costs by reducing the amount of time spent by health care workers on the administration of drugs.

In the following examples all percentages are weight by weight unless otherwise stated. The term "purified water" as used throughout the Examples refers to water that has been purified by passing it through a water filtration system. It is to be understood that the examples are for illustrative purposes only, and should not be interpreted as restricting the spirit and scope of the invention, as defined by the scope of the claims that follow.

EXAMPLE 1

Multiparticulate Modified Release Composition Containing Cyclosporine

A multiparticulate modified release composition according to the present invention comprising an immediate release component and a modified release component containing cyclosporine is prepared as follows.

(a) Immediate Release Component.

A solution of cyclosporine (50:50 racemic mixture) is prepared according to any of the formulations given in Table 1. The methylphenidate solution is then coated onto nonpareil seeds to a level of approximately 16.9% solids weight gain using, for example, a Glatt GPCG3 (Glatt, Protech Ltd., Leicester, UK) fluid bed coating apparatus to form the IR particles of the immediate release component.

TABLE 1

Immediate release component solutions

| Ingredient | Amount, % (w/w) (i) | % (w/w) (ii) |
|---|---|---|
| Cyclosporine | 13.0 | 13.0 |
| Polyethylene Glycol 6000 | 0.5 | 0.5 |
| Polyvinylpyrrolidone | 3.5 | — |
| Purified Water | 83.5 | 86.5 |

(b) Modified Release Component

Cyclosporine-containing delayed release particles are prepared by coating immediate release particles prepared according to Example 1(a) above with a modified release coating solution as detailed in Table 2. The immediate release particles are coated to varying levels up to approximately to 30% weight gain using, for example, a fluid bed apparatus.

TABLE 2

Modified release component coating solutions

| Ingredient | Amount, % (w/w) | | | | | | | |
|---|---|---|---|---|---|---|---|---|
| | (i) | (ii) | (iii) | (iv) | (v) | (vi) | (vii) | (viii) |
| Eudragit .RTM. RS 12.5 | 49.7 | 42.0 | 47.1 | 53.2 | 40.6 | — | — | 25.0 |
| Eudragit .RTM. S 12.5 | — | — | — | — | — | 54.35 | 46.5 | — |
| Eudragit .RTM. L 12.5 | — | — | — | — | — | — | 25.0 | — |
| Polyvinylpyrrolidone | — | — | — | 0.35 | 0.3 | — | — | — |
| Diethylphthalate | 0.5 | 0.5 | 0.6 | 1.35 | 0.6 | 1.3 | 1.1 | — |
| Triethylcitrate | — | — | — | — | — | — | — | 1.25 |
| Isopropyl alcohol | 39.8 | 33.1 | 37.2 | 45.1 | 33.8 | 44.35 | 49.6 | 46.5 |
| Acetone | 10.0 | 8.3 | 9.3 | — | 8.4 | — | — | — |
| Talc.sup.1 | — | 16.0 | 5.9 | — | 16.3 | — | 2.8 | 2.25 |

.sup.1 Talc is simultaneously applied during coating for formulations in column (i), (iv) and (vi).

(c) Encapsulation of Immediate and Delayed Release Particles.

The immediate and delayed release particles prepared according to Example 1(a) and (b) above are encapsulated in size 2 hard gelatin capsules to an overall 20 mg dosage strength using, for example, a Bosch GKF 4000S encapsulation apparatus. The overall dosage strength of 20 mg cyclosporine was made up of 10 mg from the immediate release component and 10 mg from the modified release component.

EXAMPLE 2

Multiparticulate Modified Release Composition Containing Cyclosporine

Multiparticulate modified release cyclosporine compositions according to the present invention having an immediate release component and a modified release component having a modified release matrix material are prepared according to the formulations shown in Table 3(a) and (b).

TABLE 3 (a)

100 mg of IR component is encapsulated with 100 mg of modified release (MR) component to give a 20 mg dosage strength product

|  | % (w/w) |
|---|---|
| IR component | |
| Cyclosporine | 10 |
| Microcrystalline cellulose | 40 |
| Lactose | 45 |
| Povidone | 5 |
| MR component | |
| Cyclosporine | 10 |
| Microcrytalline cellulose | 40 |
| Eudragit .RTM. RS | 45 |
| Povidone | 5 |

TABLE 3 (b)

50 mg of IR component is encapsulated with 50 mg of modified release (MR) component to give a 20 mg dosage strength product.

|  | % (w/w) |
|---|---|
| IR component | |
| Cyclosporine | 20 |
| Microcrystalline cellulose | 50 |
| Lactose | 28 |
| Povidone | 2 |
| MR component | |
| Cyclosporine | 20 |
| Microcrytalline cellulose | 50 |
| Eudragit .RTM. S | 28 |
| Povidone | 2 |

It will be apparent to those skilled in the art that various modifications and variations can be made in the methods and compositions of the present inventions without departing from the spirit or scope of the invention. Thus, it is intended that the present invention cover the modification and variations of the invention provided they come within the scope of the appended claims and their equivalents.

In addition, it will be apparent to those skilled in the art that cyclosporine in nanoparticulate form may be used in substitution of cyclosporine in the above examples. Further, the modified release particles may further include an additional layer of cyclosporine or nanoparticulate cyclosporine coated on top of the modified release portion, the additional layer allowing for immediate release of the cyclosporine or nanoparticualte cyclosporine.

What is claimed is:

1. A composition comprising: (a) about 50 to about 500 g/kg cyclosporine; (b) about 10 to about 70 g/kg hypromellose; (c) about 1 to about 10 g/kg docusate sodium; (d) about 100 to about 500 g/kg sucrose; (e) about 1 to about 40 g/kg sodium lauryl sulfate; (f) about 50 to about 400 g/kg lactose monohydrate; (g) about 50 to about 300 g/kg silicified microcrystalline cellulose; (h) about 20 to about 300 g/kg crospovidone; and (i) about 0.5 to about 5 g/kg magnesium stearate, wherein said cyclosporine is in a form of cyclosporine particles having an effective average particle size of less than 2000 nm in diameter, and wherein at least one surface stabilizer is associated with the surface of said particles.

2. The composition of claim 1, further comprising a coating agent.

3. A composition comprising the following components: (a) about 100 to about 300 g/kg cyclosporine; (b) about 30 to about 50 g/kg hypromellose; (c) about 0.5 to about 10 g/kg docusate sodium; (d) about 100 to about 300 g/kg sucrose; (e) about 1 to about 30 g/kg sodium lauryl sulfate; (f) about 100 to about 300 g/kg lactose monohydrate; (g) about 50 to about 200 g/kg silicified microcrystalline cellulose; (h) about 50 to about 200 g/kg crospovidone; and (i) about 0.5 to about 5 g/kg magnesium stearate, wherein said cyclosporine is in a form of cyclosporine particles having an effective average particle size of less than 2000 nm in diameter, and wherein at least one surface stabilizer is associated with the surface of said particles.

4. The composition of claim 3, further comprising a coating agent.

5. The composition of claim 1 or 3 formulated into a dosage form selected from the group consisting of liquid dispersions, gels, aerosols, ointments, creams, controlled release formulations, fast melt formulations, lyophilized formulations, tablets, capsules, delayed release formulations, extended release formulations, pulsatile release formulations, and mixed immediate release and controlled release formulations.

6. The pharmaceutical composition according to claim 1 or 3 of comprising solid particles cyclosporin coated with one or more surface stabilizers, wherein the particles have an average effective particle size of from about 50 nm to less than 2 microns and wherein the composition is a pharmaceutical composition.

7. The composition of claim 6, wherein the surface stabilizer is selected from the group consisting of: anionic surfactants, cationic surfactants, zwitterionic surfactants, nonionic surfactants, surface active biological modifiers, and combinations thereof.

8. The composition of claim 7, wherein the anionic surfactant is selected from the group consisting of: sodium lauryl sulfate, sodium alginate, sodium carboxymethylcellulose, and calcium carboxymethylcellulose.

9. The composition of claim 6 wherein the cationic surfactant is selected from the group consisting of quaternary ammonium compounds, benzalkonium chloride, and lauryldimethylbenzylammonium chloride.

10. The composition of claim 6, wherein the surface stabilizer is a pegylated phospholipid.

11. The composition of claim 6, wherein the nonionic surfactant is selected from the group consisting of polyoxyethylene sorbitan fatty acid esters, polyoxyethylene fatty acid esters, sorbitan esters, glycerol monostearate, polyethylene glycols, cetyl alcohol, cetostearyl alcohol, methylcellulose, hydroxy propylcellulose, hydroxy propylmethylcellulose, polysaccharides, starches, starch derivatives, and polyvinylpyrrolidone.

12. The composition of claim 7, wherein the surface active biological modifier is selected from the group consisting of proteins, polysaccharides, and combinations thereof.

13. The composition of claim 12, wherein the polysaccharide is selected from the group consisting of starches and chitosans.

14. The composition of claim 12, wherein the protein is casein.

15. The composition of claim 6, further comprising a pH adjusting agent.

16. The composition of claim 15, wherein the pH adjusting agent is selected from the group consisting of succinic acid and citric acid.

* * * * *

UNITED STATES PATENT AND TRADEMARK OFFICE
CERTIFICATE OF CORRECTION

PATENT NO. : 7,825,087 B2
APPLICATION NO. : 11/568692
DATED : November 2, 2010
INVENTOR(S) : Scott A. Jenkins et al.

It is certified that error appears in the above-identified patent and that said Letters Patent is hereby corrected as shown below:

At column 34, claim number 9, line number 38, please delete "The composition of claim 6" and replace it with --The composition of claim 7--.

At column 34, claim number 11, line number 44, please delete "The composition of claim 6" and replace it with --The composition of claim 7--.

Signed and Sealed this
First Day of February, 2011

David J. Kappos
*Director of the United States Patent and Trademark Office*